United States Patent [19]
Tomlin

[11] Patent Number: 5,473,951
[45] Date of Patent: Dec. 12, 1995

[54] DIFFERENTIAL DILUTION SAMPLING PROBE

[76] Inventor: Robert L. Tomlin, Rte. 3, Box 127, Waldron, Ark. 72958

[21] Appl. No.: 264,335

[22] Filed: Jun. 23, 1994

[51] Int. Cl.[6] .................................................. G01N 1/00
[52] U.S. Cl. ........................................................ 73/863.83
[58] Field of Search ............................. 73/1 G, 23.31, 73/863.01–863.03, 863.11, 863.23, 863.83, 864.34, 864.73, 864.81

[56] References Cited

U.S. PATENT DOCUMENTS

| | | | |
|---|---|---|---|
| 3,407,646 | 10/1968 | Traver | 73/23.31 |
| 3,892,549 | 7/1975 | Lyshkow . | |
| 3,901,672 | 8/1975 | Roberts . | |
| 4,856,352 | 8/1989 | Daum et al. | 73/1 G |
| 4,974,453 | 12/1990 | Hohorst | 73/863.11 |
| 5,058,440 | 10/1991 | Graze, Jr. | 73/863.83 |
| 5,109,708 | 5/1992 | Lawless | 73/863.11 |
| 5,237,881 | 8/1993 | Ross . | |
| 5,297,432 | 3/1994 | Traina et al. | 73/863.83 |

Primary Examiner—Robert Raevis
Attorney, Agent, or Firm—Dennison, Meserole, Pollack & Scheiner

[57] ABSTRACT

A method and apparatus for sampling and dilution of a process gas stream. A probe is inserted into the stream, the probe being open at its front end, and a precisely regulated flow of a dilution gas is inputted at a mid-point of the probe. A precisely regulated, and greater flow of unfiltered gas is withdrawn from the rear end of the probe. The difference between the input flow and the withdrawn flow is process gas which is diluted by the dilution gas, and the ratio of process gas to withdrawn flow can be precisely regulated.

24 Claims, 4 Drawing Sheets

DIFFERENTIAL DILUTION SAMPLING PROBE

BACKGROUND OF THE INVENTION

This invention relates to a process and apparatus for sampling the content of industrial process gas streams, in which a portion of the process gas stream is extracted, conditioned for analysis, and transported to a gas analysis device. Such a system is disclosed, for example, in U.S. Pat. No. 4,738,147.

Due to the trend in government regulations to require the measurement of gases not measured in the past, such as $Cl_2$, $ClO_2$, NCl, $NH_3$ and other toxic gases, a clear need exists for a sampling and analysis system that will permit the measurement of these highly reactive gases without loss in the extraction and conditioning stages.

Many gas analysis systems are exposed to a mixture of gases. However, gases other than the gas or gases of interest may cause an erroneous response in the analysis system. In the past, dilution of the process gas stream with air has been demonstrated as a reliable way to achieve lower concentrations of the interfering gas and to eliminate many interference problems. Dilution of the process gas has also been shown to be a reliable way to make the gas more transportable through long sample lines, filters and other sample system components.

Several dilution and sampling systems have been developed that have proven to be adequate for monitoring the normal compliance gases such as $SO_2$, $NO_x$, TRS, CO, etc. The known dilution systems, however, experience sample loss problems when attempting to measure the more reactive gases mentioned above. The primary reason for this difficulty is that existing dilution systems force the raw process gas to flow over a filter element and then through a critical orifice before dilution occurs. This is disclosed, for example, U.S. Pat. No. 5,178,022. Forcing the raw process gas to contact the filter media at the high humidity and high concentration levels as extracted from the process causes the more reactive gases to be lost to reactions on the filter surface. In some cases, the sample may be lost in unwanted reactions with other process stream components while flowing through the sample probe before even reaching the external filter and dilution system.

A diagram of a first typical dilution probe is shown in FIG. 1. All of the system components are contained in a stainless steel pipe 10, which is inserted into the process environment. The coarse filter 12, restrictor plate 14, fine filter 16, glass orifice 18, stainless steel tube fitting 20, and eductor assembly 22 are all subject to process temperature extremes between 35° and 1200° F. The stability of the critical components and the ultimate dilution ratio stability are extremely difficult to control under the widely changing process conditions. Attempts have been made to control the temperature of the probe body to reduce the effects of changing process temperatures but have met with limited success due to the wide range of possible temperatures and the highly corrosive environments of the process streams.

A further problem with the existing technology is the inability to calibrate through the first or coarse filter 12. Although this filter consists of only a stainless steel screen, in most cases substantial loss may be caused by this filter if the filter is allowed to become wet or partially plugged with a reactive particulate from the process. It can be seen that the sample gas must pass through two filter elements 12 and 16, a quartz orifice assembly 18 and a stainless steel tube fitting 20 before being diluted in the eductor assembly 22. Because the fine filter is exposed to the full process temperature, polymer filters which are compatible with gases such as $Cl_2$, $ClO_2$ and HF cannot be used. Instead, glass fiber filters must be used, and these filters are more reactive with the process gases.

Another known dilution probe 26 is shown in FIG. 2. This probe design moves the critical flow components out of the stack environment by utilizing a long sampling pipe 28, typically 4 to 10 feet long. However, this probe still requires that the process gas pass through a filter element 30 and a critical orifice 32 before dilution. The process gas, in many cases, is cooled in passage to the filter element because the pipe 28, is not maintained at the process temperature. This cooling has been shown to cause a loss of reactive gases such as ammonia before even reaching the external filter element. Also, the long probes are a problem due to the long response times that are caused by the combination of large internal volume and low flow rates.

This probe design may also experience a problem of sample loss when used on liner stacks. Liner stacks are usually large stacks that are supported by an outer concrete stack. Sampling systems are sometimes mounted on these stacks such that the sampling probe extends from the hot stack through a cool zone between the inner and outer stack and then into the sampling system. Cooling of the gas in the probe, in this cool zone, shown as zone 34 in FIG. 2, can cause severe loss of sample due to condensation and other gas reactions inside the pipe. Attempts to heat the probe in these cool zones has had limited success, but is costly and increases the maintenance requirements.

SUMMARY OF THE INVENTION

It is therefore an object of the invention to provide a gas sampling and analysis system that allows accurate and interference free measurement of process gas streams for highly reactive gases that could not be reliably measured in the past, while satisfying all of the requirements of the Environmental Protection Agency.

It is a further object of the present invention to provide a gas sampling and analysis system that provides the speed of response and application versatility of in situ dilution probes and the ease of maintenance and accurate calibration features of low flow external dilution probes while allowing the measurement of highly reactive gases that cannot be reliably measured by any existing dilution system.

Thus, the invention solves the problems of the prior art by utilizing a technique that dilutes the stack gas inside the process stack, at process temperature, before the gas contacts any filter or any sampling system component that would cause sample loss. This dilution is accomplished by a flow difference technique. An air aspirator and critical orifice assembly, or a mechanical pump, pulls a precise and known total flow of gas through a probe. By introducing an equally precise and known flow of clean dry air to a location near the front of the probe, at a flow rate slightly less than the total flow, a precise and known amount of process gas will be withdrawn form the process and diluted by the air. The quantity of process gas withdrawn and thus the dilution ratio may be easily adjusted by changing the air flow rate, the total flow rate, or both flow rates. This technique allows the process gas to be diluted to lower concentration levels while the process gases are still under process conditions and before contacting any filtering device.

A dilution ratio of about 10:1 will typically be accomplished at this point, as this dilution makes the more reactive gases much easier to transport. Other dilution ratios from 1:1 to 100:1 are also possible. If further dilution is required, this may be accomplished in a remote aspirator that pulls the total flow or adding additional air at the output of the pump.

Diluting the process gas in this manner has several important benefits:

1) A wider range of process gases may be measured because no filter contacts the gas before dilution. The dilution occurs in mid air and causes the process gas to be diluted to a lower, more transportable level before leaving the process conditions.

2) The filter body, filter, and eductor may be fabricated of lower temperature and highly inert materials, i.e. fluoropolymers, polysulfones, and poly amide-imides. Using these materials, with a dilute process gas, greatly reduces the possibility of unwanted gas reactions with the sampling system components and provides much greater accuracy and stability in difficult or extremely corrosive applications.

3) Much longer filter life is possible with this design because the sampling system pulls typically one-fourth to one-tenth the flow from the process than existing sampling systems. While existing dilution systems could pull these low flows, response times and sample loss would rise to unacceptable levels due to the long transport time of the undiluted process gas down the probe barrel. By accomplishing a differential dilution near the probe tip, very small quantities of process gas may be used while maintaining system response times faster than conventional extractive dilution probes.

4) Because the process gas is diluted near the probe tip, problems associated with loss in the probe barrel due to sample cooling can be greatly reduced or completely eliminated in some cases. This probe design is more useful with liner stacks by eliminating the need to heat the probe, and allows for the measurement of many gases not possible with conventional sampling systems.

DESCRIPTION OF THE PREFERRED EMBODIMENTS

The differential dilution sampling probe and system have been developed to provide a means to reliably extract and measure highly reactive gases that cannot be measured by existing sampling systems. This same method may also be used for gases that are not reactive. Because the sampled gases are made less reactive by this dilution inside the process stack or stream, many of the components that comprise the sampling system can be fabricated from lower cost materials and therefore may provide a lower cost and highly reliable alternative to existing sampling systems. Once the gases are made less reactive and easier to transport, many opportunities exist for the design of gas analysis systems using this technique.

Figure 1:
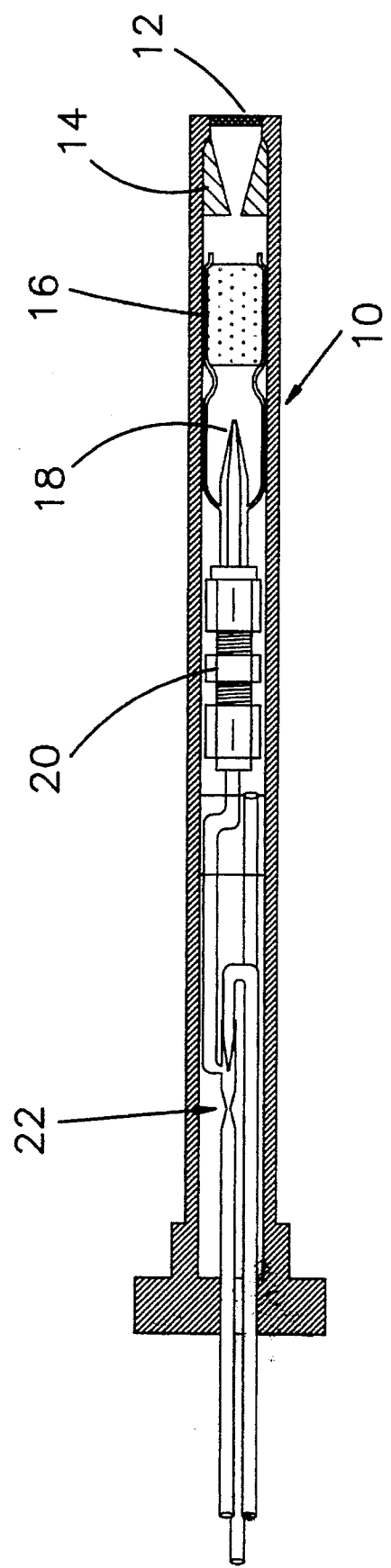
FIG. 1 is a cross-sectional view of a first prior art probe.
Figure 2:
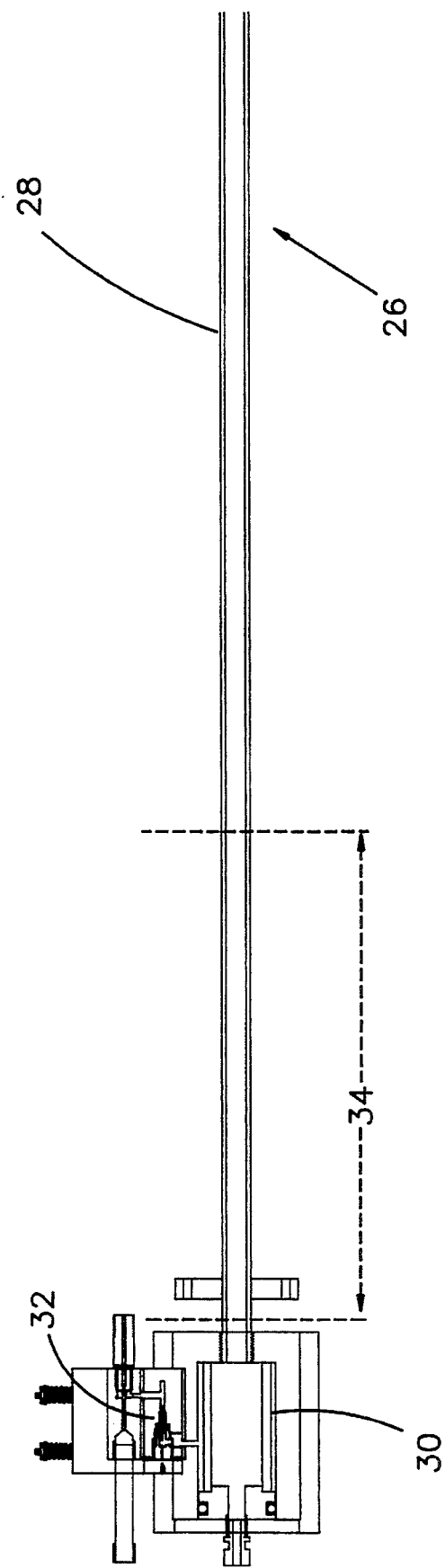
FIG. 2 is a cross-sectional view of a second prior art probe.
Figure 3:
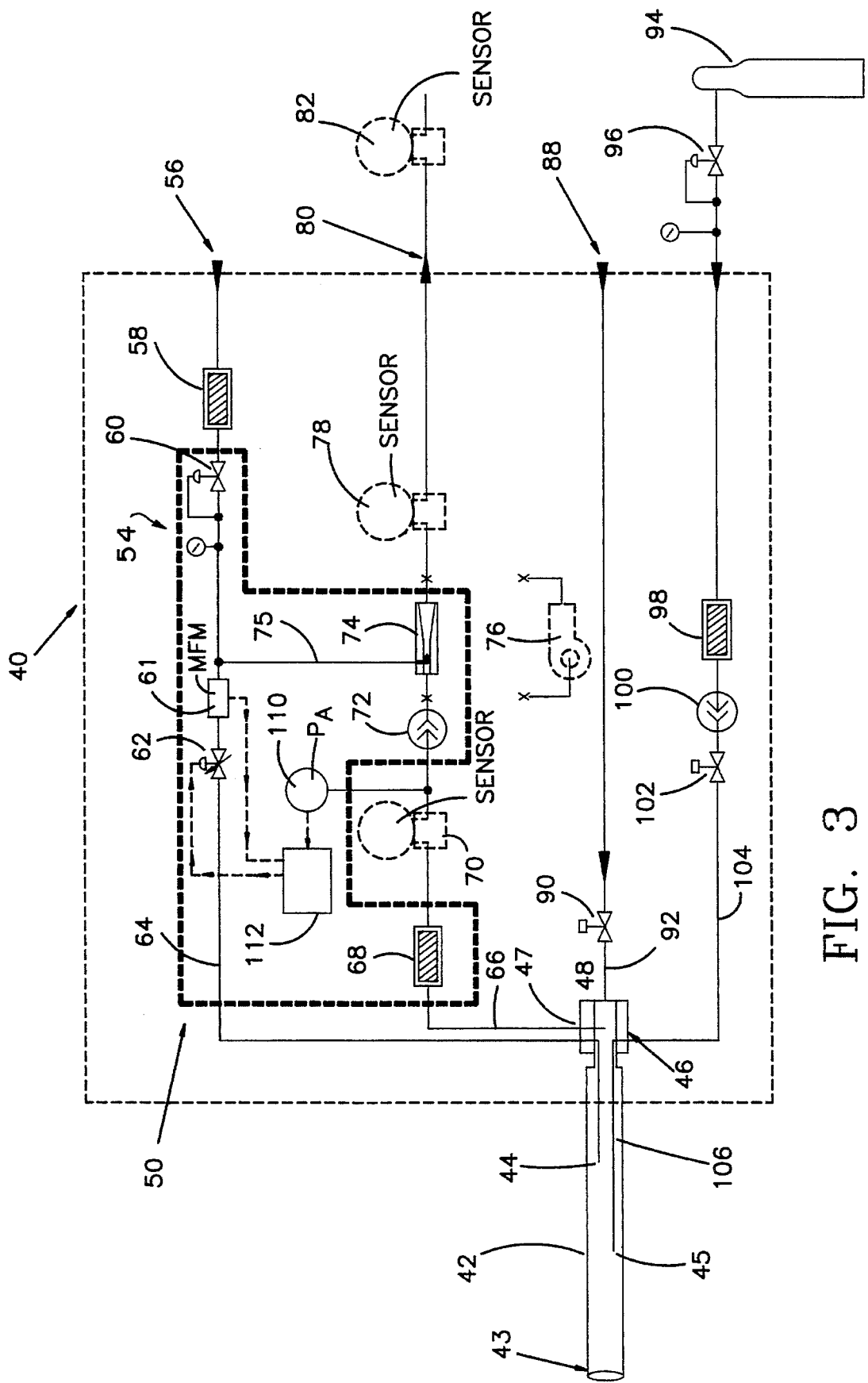
FIG. 3 is a schematic diagram of a differential dilution probe and system according to the invention.
Figure 4:
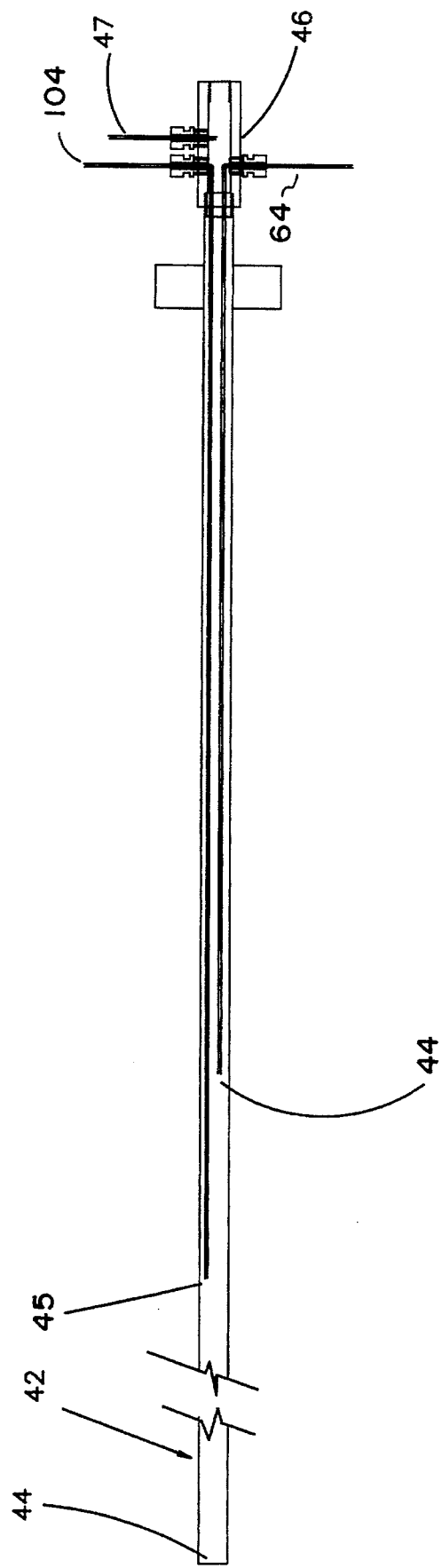
FIG. 4 is a cross-sectional view of one embodiment of the probe shown in FIG. 3.

The sampling system 40 of the invention, as shown in FIGS. 3 through 5, includes a probe 42 and a differential flow assembly 50 shown within the heavy dotted lines. The probe assembly 42 may be fabricated from any material compatible with the process gases and process conditions. Typical materials would be Hastelloy C-276, 316 stainless steel, Teflon and ceramics. For best response and minimum loss, it is recommended that for process sample flow rates between 10 and 50 ml/min, a probe of 0.540" O.D. and 0.302" I.D. should be used, and for process sample flow rates between 50 and 250 ml/min, a probe of 0.675" O.D. and 0.493" I.D. be used. Depending on process conditions, the inner diameter of the probe may vary between 0.125" and 0.500".

The probe includes a tip 43, a dilution gas inlet 44, and a calibration gas inlet 45. The rear portion of the probe includes a block 46 for interface with the remainder of the sampling system, block 46 including a sample gas outlet 47 and a blowback inlet 48. Interface block 46 may be integral with the probe, or may be a separate unit attached to the probe, as shown in FIG. 4.

The differential flow system 50 includes an inlet 56 for dilution gas such as clean, dry air, and a particulate filter 58 for filtering the air. The air supply system further comprises a pressure regulator 60, mass flow meter 61, control valve 62 and a line 64 which flows from the control valve to the interface block where it connects with dilution gas inlet 44.

Sample gas outlet 47 in the interface block is connected by line 66 to a heated filter 68. The outlet from the filter 68 may be provided to a gas sensor 70, although sensor 70 is usually omitted and the gas passed directly to a critical orifice 72. Connected in the gas transport line after critical orifice 72 is a precision means for drawing gas through the system. This precision means may be eductor 74 as shown connected to the system connected to the dilution gas inlet by line 75, or may be a precision pump 76, shown in phantom lines in FIG. 3, which may replace eductor 74. Another sensor 78 may be located within the sampling system housing downstream of the eductor or pump, or the sample gas may be withdrawn at port 80 and passed continuously or intermittently to an additional sensor 82.

A blowback system is also provided for the probe, including a gas inlet 88 and valve 90.

A calibration system is further provided for calibrating the sampling system, the calibration system including calibration gas source 94, regulating valve 96, filter 98, critical orifice 100, and regulating valve 102, the calibration gas connected through line 104 to calibration gas outlet 45 in the probe.

The following description will describe the normal sampling mode of operation for one proposed system according to the invention shown in FIGS. 3 and 4, the calibration mode for this system, and the blowback mode for this system and will discuss several possibilities for connection of the sampling system to existing gas analyzers.

NORMAL SAMPLING MODE

Process enters the sampling system 40 at the tip 43 of probe 42. For purposes of discussion, a dilution ratio of 10:1 will be described. A low flow rate of the process gas enters the probe 42 and travels down the probe barrel to dilution gas inlet 44.

Due to the low flow rate, approximately 95% of the particulate matter greater than 5 microns in diameter, drops out on the wall of the probe before reaching inlet point 44.

At inlet 44, a precise flow of clean dry air is introduced, supplied from a differential flow assembly 50. Air is introduced to the assembly at inlet 56, flows through a particulate filter 58 and then into a precision air pressure regulator 60. The pressure regulator 60, mass flow meter 61 and electronic flow control valve 62 are part of differential flow assembly 50 contained in a temperature regulated casing or block kept at 150° F. From control valve 62 the air flows through line 64 through interface block 46 and exits into the probe interior at inlet 44. Because the critical orifice 72 and the prime mover for the sample (either air aspirator 74 or mechanical pump 76) transport a diluted sample, instead of raw process gas, there is no longer a need to heat these components to high temperatures (300° to 600° F.) to prevent acid gas condensation. The differential dilution block 50 and the components contained within the block are heated only to a temperature slightly above the highest expected ambient temperature to allow precise temperature control of these components. This ability to operate the sample prime mover at a lower temperature allows mechanical pumps to be used, provided that the sampled gas does not react with the pump materials of construction (usually 316 stainless steel and teflon). This also allows the use of low cost sensors (electrochemical, IR etc.), that do not require additional dilution, to be inserted in line at 78. This is important because these sensors are very sensitive to process pressure and cannot be operated at point 70 and, due to the lack of sensitivity, could not be used at point 78 if an air aspirator were used because of the added dilution caused by the aspirator. Using a mechanical pump allows the sensor to be placed at 78, without further dilution of the sample, while completely isolating the sensor from process pressure changes.

A total probe flow is established by a critical orifice 72 and air aspirator 74 if additional dilution of the sample is required, or by critical orifice 72 and a mechanical pump 76 is additional dilution is not required. For a 10:1 dilution ratio orifice 72 would be selected to give a flow of 250 cc/min. and control valve 62 would be adjusted to give an air flow of 225 cc/min. A differential flow of 25 cc/min. would be pulled from the process and mix with the 225 cc/min. from control valve 62. The total flow of 250 cc/min. would then flow through probe 42 through interface block 48 through line 66 and into heated filter 68 located in the differential flow assembly 50. Upon reaching point gas inlet 44 in the probe, the process gas is diluted 10:1 by the precise flow of air supplied. The process gas at this point has been diluted without having passed through a filter or flow controlling device.

It is not necessary to heat filter 68 to high temperatures to avoid sample loss. Heating the filter to approximately 150° F. ensures that the filter element stays dry and non-reactive. This lower temperature allows the use of porous polymer membrane filters that are, in many cases, much less reactive with the sample gas. The filter housing 68 is located on the differential dilution block 50. If a sampled gas requires more dilution than is provided by the differential dilution inside the probe, as would be the case if the sample gas were to be transported to a remote analyzer location 86, or for analyzers requiring a very dilute sample (IMS, fluorescent, chemiluminescent etc), then additional dilution can be provided by air aspirator 74 or by adding air into the outlet side of the mechanical pump 76. Dilution ratios for the combined system could range from 1:1 to 1000:1 (10:1 differential dilution ×100:1 at the aspirator 74). The benefits of differential dilution would likely be lost at a 1:1 ratio but it is an adjustment possibility.

The differential dilution technique is very sensitive to conditions that would change the flow rate of either the air flow through control valve 62 or orifice 72. For example, a 1% change in the flow through orifice 62 is amplified by the dilution ratio and becomes a 10% change in concentration supplied to the sensors. The flow rates are primarily affected by the temperature of the flow control components and by the absolute pressure appearing on the upstream side of orifice valve 62. Valve 62 is operated with a differential vacuum of 20 mm Hg and, due to the characteristics of a critical orifice operated under these conditions, provides a flow that is unaffected by small changes in vacuum. All components in differential flow block 50 are heated to 150°±0.5° F.

The other significant variable that could affect the dilution ratio is the absolute pressure appearing on the upstream side of orifice 72. To precisely regulate the dilution ratio, the system provides electronic control apparatus 112, valve 62 with electronic control and mass flow meter 61, these elements precisely controlling the dilution ratio in response to absolute changes appearing at the upstream side of orifice 72. As an example, if a pressure change occurred either in the process or in barometric pressure, this absolute pressure change would be sensed by orifice 72 and absolute pressure transducer 110. This pressure change could cause the flow through orifice 72 to change by 1%, for example. The signal from the absolute pressure transducer 110 is conditioned by electronic control 112, that in turn sends a signal to control valve 62. The control board is calibrated such that a signal is output to control valve 62 that causes an air flow change of 1% to occur which returns the dilution ratio to the same value as before the pressure change occurred. By controlling the variables that effect the flow rates in this manner, the dilution ratio can be held to within 7% in 24 hours with a changing ambient temperature and process or barometric pressure changes.

BLOWBACK MODE

The probe 42 is cleaned periodically by introducing high pressure blowback air through inlet 88, blowback solenoid valve 90, and through line 92 into interface block 46, through probe 42 and exiting into the process at probe tip 43. Solenoid valve 90 may be operated either automatically or manually. The preferred method would be to automatically energize solenoid valve 90 with either a local timer or a remote controller. The interval between blowbacks may vary between 15 minutes for the most extreme applications and several hours for cleaner applications.

CALIBRATION MODE

The differential dilution sampling probe assembly is calibrated by passing a gas of known concentration through all of the components in the sample analysis system that the process gas would flow through and adjusting the response of the gas analysis system to equal the value of the known calibration gas. Calibrating in this manner allows for compensation of the total system for losses in filter elements or other pneumatic components, changes in dilution air flow rates and changes in process gas flow rates.

In order to calibrate the system, the calibration gas flows from cylinder 94 through regulator 96, through orifice protection filter 98, and through orifice 100 to solenoid valve 102. Solenoid valve 102 allows the flow of calibration gas to be initiated either locally or remotely by a remote controller. The calibration valve is located physically above interface block 46 to prevent condensation from forming in the calibration lines between calibrations. From solenoid valve 102, the calibration gas passes through line 104, through the interface block 46, through line 106 and flows into the probe exiting at point 45. The flow rate of the calibration gas is set to be at least 1.5 times the process flow being pulled at probe tip 43. The flow rate of the calibration gas is not critical because the differential dilution probe will pull the same flow of calibration gas as was being pulled from the process. Excess calibration gas would exit into the stack at probe tip 43.

What is claimed is:

1. An apparatus for sampling and dilution of a process gas, comprising:

probe means comprising a body portion adapted for insertion into a process gas stream and having first and second ends, said first end being open and comprising an inlet for process gas, and a closed interface block at said second end of said body portion, closing said second end;

a differential flow assembly comprising means for supplying a precisely regulated flow of dilution gas to said probe means, and means for withdrawing a precisely regulated flow of diluted gas from said probe means which is greater than the flow of dilution gas;

a dilution gas inlet means comprising a tube passing through said interface block into said body portion and terminating at a point located between said first and second ends and flow connected through said interface block to said means for supplying dilution gas;

a diluted gas outlet within said probe means and located closer to said second end than said dilution gas inlet means, said diluted gas outlet flow connected to said means for withdrawing;

means for passing diluted gas from said means for withdrawing to an analysis device.

2. Apparatus according to claim 1, additionally comprising means for regulating the temperature of the differential flow assembly.

3. Apparatus according to claim 1, additionally comprising means for providing blowback gas connected to said second end for cleaning said probe means.

4. Apparatus according to claim 1, additionally comprising means for providing calibrating gas connected to said probe means between said first end and said dilution gas inlet.

5. Apparatus according to claim 1, wherein said means for supplying a precisely regulated flow comprises a precision gas flow regulator.

6. Apparatus according to claim 1, wherein said means for withdrawing comprises a critical orifice means and a gas mover means flow connected downstream of said critical orifice means.

7. Apparatus according to claim 6, wherein said gas mover means comprises an aspirator means which further dilutes gas moved therethrough.

8. Apparatus according to claim 6, wherein said gas mover means comprises a pump.

9. Apparatus according to claim 6, wherein said differential flow assembly additionally comprises means for determining the absolute pressure upstream of said critical orifice means, and means for regulating said means for supplying in response to changes in the absolute pressure.

10. Apparatus according to claim 1, additionally comprising an analysis means in flow connection with said means for passing.

11. A dilution probe for sampling process gas comprising:

a probe comprising a generally cylindrical body portion having first and second ends, said first end being open for withdrawal of gas from a process stream;

a closed interface block at said second end of said body portion, closing said second end;

dilution gas supply means comprising a supply tube extending through said interface block into said body portion, and terminating in a gas inlet between said first and second ends; and diluted gas outlet means comprising a withdrawal tube passing through said interface block and terminating in a gas outlet located closer to said second end than said dilution gas inlet;

wherein the body portion between said dilution gas inlet and said diluted gas outlet serves as a mixing zone for mixing process gas and dilution gas, and no filtration means are located between said first end and said second end.

12. Probe according to claim 11, additionally comprising inlet means for blowback gas located in said second end.

13. Probe according to claim 11, additionally comprising inlet means for calibration gas locating between said first end and said dilution gas inlet means.

14. Probe according to claim 13, wherein said calibration gas inlet means and said dilution gas inlet means extend through said interface block and into said probe body.

15. Probe according to claim 11, wherein said interface block comprises a separate unit in flow connection with said second end which serves to close said second end.

16. Method for sampling and dilution of a process gas from a process gas stream, comprising:

a) extending into the stream a probe having a first open end and a second closed end, said first end being within said stream;

b) providing a precisely regulated flow of dilution gas at a first point between said first end and said second end, said first point being at a probe portion within said process stream, and simultaneously withdrawing a precisely regulated gas flow from a second point between said first point and said second end without filtering said gas flow between said open end and said second point, said gas flow withdrawn being greater than said dilution gas flow, thus causing a known flow of process gas to mix with said dilution gas flow and be withdrawn at said second point; and c) providing said withdrawn gas flow for analysis.

17. Method according to claim 16, wherein the ratio of known process gas flow to dilution gas flow is from 1:1 to 1:100.

18. Method according to claim 17, wherein said ratio is from 1:5 to 1:20.

19. Method according to claim 18, wherein said ratio is 1:10.

20. Method according to claim 16, wherein said withdrawn gas flow is withdrawn by aspiration, which further dilutes the withdrawn gas.

21. Method according to claim 16, additionally comprising measuring the absolute pressure of the withdrawn gas, and adjusting the dilution gas flow based on the absolute pressure, so as to maintain a constant ratio of dilution gas to withdrawn gas.

22. Method according to claim 16, additionally comprising terminating both said dilution gas flow and said withdrawn gas flow, and blowing a gas from said second end to said first end to clean said probe.

23. Method according to claim 16, additionally comprising introducing a flow of a known calibrating gas between said first end and said first point 24. Method according to claim 23, wherein the calibration gas flow is at least 1.5 times said known flow of process gas.

* * * * *